United States Patent [19]
Carr

[11] Patent Number: 5,094,617
[45] Date of Patent: Mar. 10, 1992

[54] DENTAL RETRO-FILLING PREPARATION TOOL AND METHOD

[76] Inventor: Gary B. Carr, 273 Church Ave., Chula Vista, Calif. 92010

[21] Appl. No.: 625,360

[22] Filed: Dec. 11, 1990

[51] Int. Cl.$^5$ ............................................... A61C 1/07
[52] U.S. Cl. ................................... 433/119; 433/165; 433/224
[58] Field of Search ................. 433/102, 118, 119, 81, 433/165, 166, 224, 86, 124, 125, 141

[56] References Cited

U.S. PATENT DOCUMENTS

| | | | |
|---|---|---|---|
| 1,067,015 | 7/1913 | Fowler | 433/102 |
| 3,133,351 | 5/1964 | von Seggern | 433/119 |
| 3,703,037 | 11/1972 | Robinson | 433/86 |
| 4,330,278 | 5/1982 | Martin | 433/86 |

OTHER PUBLICATIONS

"Surgical Endodontics" by James L. Gutmann and John W. Harrison, published by Blackwell Scientific Publications, 1991, pp. 222 to 226.

Primary Examiner—Cary E. O'Connor
Attorney, Agent, or Firm—Brown, Martin, Haller & McClain

[57] ABSTRACT

A drilling tool for dental retro-filling preparation comprises an ultrasonic transducer head and one or more elongate drill members for selectively securing to the transducer head. The or each drill member comprises an elongate shaft having a suitable securing mechanism at one end for coupling to the transducer head and a hooked portion at the opposite end comprising the drilling tip which projects at an angle to the remainder of the shaft. The hooked end portion of the shaft is inserted through an appropriate opening in the jawbone until it is located adjacent the tooth root and aligned with the axis of the root, and the transducer head is switched on to cause ultrasonic vibrations in the tip which cut a bore in the tooth root.

14 Claims, 1 Drawing Sheet

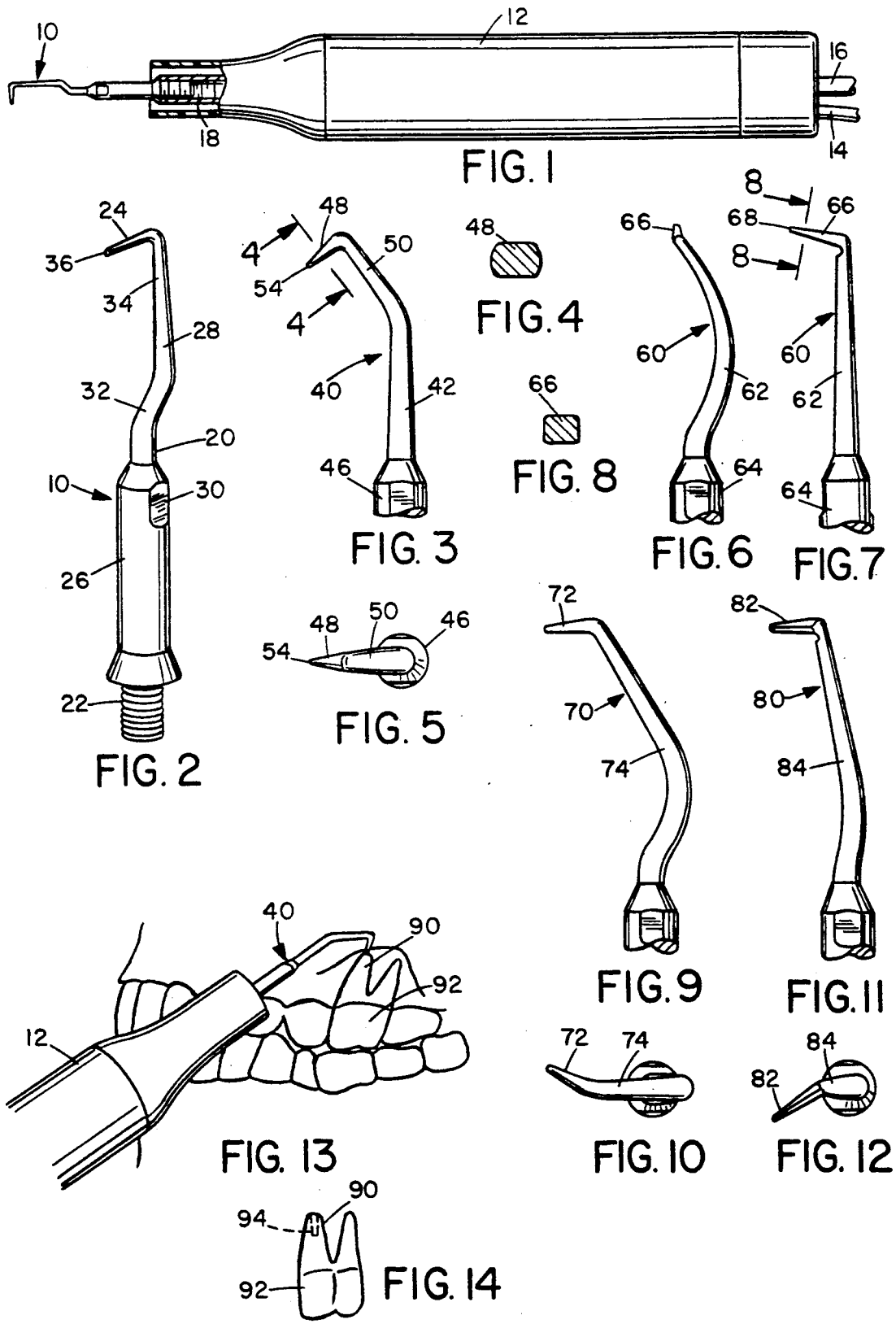

DENTAL RETRO-FILLING PREPARATION TOOL AND METHOD

BACKGROUND OF THE INVENTION

The present invention relates generally to an apparatus and method for preparing dental retro-fillings, or drilling bores into the roots of teeth.

In root canal surgery, an opening is drilled into a tooth from the top, revealing the space containing the pulp. The pulp is then removed, and the entire internal area of the tooth is filled with a suitable rubber filler material. However, this is sometimes not sufficient to deal with the problem, and the patient continues to feel pain in the tooth. In this event, the dental surgeon must drill into the bottom of the tooth root in the jawbone to remove the bottom of the root, and removing the abcess. An opening must be cut in the side of the jawbone to gain access to the tooth root. The tip of the root is then removed. The next step in root canal surgery is a so-called retro-filling, in which a reverse cylindrical bore is cut into the bottom of the root, and filled wtih a filling material. The making of the necessary reverse cylindrical bore requires the cutting of a fairly large hole in the jawbone to gain access to the tooth, under current procedures.

Existing tools used by dentists to drill bores in the roots of teeth for retro-filling comprise a handpiece having an end portion from which a short, rotary drill bit projects perpendicularly. The size of the handpiece makes it difficult to gain access to the root without cutting a large opening in the jawbone, and it is also difficult to ensure that the bore extends parallel to the central longitudinal axis of the root using the existing tool, since the drill bit has a tendency to wobble and can even destroy the root completely in some cases.

SUMMARY OF THE INVENTION

It is an object of this invention to provide a new and improved apparatus and method for preparing dental retro-fillings in root canal surgery.

According to one aspect of the present invention, a tool for preparing bores in the bottom of a tooth root is provided which comprises a vibrating member comprising an elongate shaft, a securing mechanism such as screw threads at one end of the shaft for coupling it to an ultrasonic vibrator device, and a hooked portion at the opposite end of the shaft, the hooked end portion of the shaft being pointed and extending at an angle to the remainder of the shaft for access to the bottom of a tooth root through the side of the jawbone.

The securing mechanism will be dependent on the type of coupling provided on the ultrasonic device on which the tool is to be mounted, and may comprise a screw-threaded bore or post, for example.

The hooked end of the shaft may be a circular or non-circular cross-section to produce a bore of similar cross-section in the bottom of the tooth root, in order to increase the retention factor. For example, the tip may be of square or flattened circular cross-section. Preferably, at least two different drill members are provided for use in different areas of the mouth, one of the drill members having a hooked end which is co-planar with the remainder of the shaft and the other drill member having an offset hooked end at an angle to the plane of the remainder of the shaft. The first type is for use in front areas of the mouth while the second type can be used in posterior areas, enabling the tool to be held at an angle by the surgeon while the tip is presented in the correct orientation for drilling parallel to the longitudinal axis of the tooth root. This will also allow parallel retro-preparations in severely inclined teeth.

The drill piece or member is preferably designed to be mounted in an ultrasonic transducer head having a threaded bore or post for coupling with the threaded end of the shaft. Such ultrasonic transducers are often used for tooth cleaning purposes.

This apparatus enables a dental retro-filling to be prepared via a smaller opening in the jawbone than was previously necessary wtih conventional techniques, and also enables a deeper, more parallel and more accurate preparation than was previously possible.

According to another aspect of the invention, a method of drilling a bore in the lower end of a tooth root to receive a retro-filling is provided, which comprises the steps of cutting an opening in the jawbone at the location of the tooth root to be drilled, attaching an elongate drill member having a hooked end to an ultrasonic transducer head, inserting the hooked end of the drill member through the opening in the jaw bone and aligning it with the central longitudinal axis of the root, and activating the transducer head to vibrate the hooked end of the drill member and drill a corresponding bore in the end of the root.

BRIEF DESCRIPTION OF THE DRAWINGS

The present invention will be better understood from the following detailed description of some preferred embodiments, taken in conjunction with the accompanying drawings, in which like reference numerals refer to like parts, and in which:

FIG. 1 is a side elevation view of a typical ultrasonic hand tool with a tip in place;

FIG. 2 is an enlarged perspective view of one configuration of the tip;

FIG. 3 is a side elevation view of another form of the tip;

FIG. 4 is an enlarged sectional view taken on line 4—4 of FIG. 3;

FIG. 5 is a top plan view of the tip of FIG. 3;

FIG. 6 is a side elevation view of another form of the tip;

FIG. 7 is a front elevation view of the tip of FIG. 6;

FIG. 8 is an enlarged sectional view taken on line 8—8 of FIG. 7;

FIG. 9 is a side elevation view of a further form of the tip;

FIG. 10 is a top plan view of the tip of FIG. 9;

FIG. 11 is a side elevation view of another form of the tip;

FIG. 12 is a top plan view of the tip of FIG. 11;

FIG. 13 illustrates one use of the tip in a retro-prep operation; and

FIG. 14 illustrates a prepared tooth.

DESCRIPTION OF THE PREFERRED EMBODIMENT

FIG. 1 of the drawings illustrates a retro-bit or member 10 according to one embodiment of the present invention attached to a typical ultrasonic dental hand tool or transducer head 12 of a type commonly used in conjunction with cleaning tips to remove calculus from crowns, fillings and the like and to clean teeth. The transducer head 12 may, for example, comprise an Amadent ultrasonic unit or an Osada SE 04 ultrasonic transducer, or equivalent transducer heads containing a piezo-electric ultrasound unit. These transducer heads have electrical input leads 14 and a water inlet 16 at one end, and a coupling at the opposite end for securing a selected tool to the head to be vibrated. In the illustrated embodiment, the coupling comprises a mounting bore 18 having screw threads for securing to corresponding screw threads on a selected tip. However, it will be understood that other securing mechanisms may be used in alternative arrangements, with the drill tips being provided wtih appropriate securing configurations for mating engagement with corresponding formations on the ultrasonic transducer head wtih which they are to be used. For example, other transducer heads have a threaded projection for engagement in a corresponding threaded bore.

FIGS. 2 to 12 of the drawings illustrate several drill tips or members of various configurations which may be secured to the transducer head 12 in order to prepare a dental retro-preparation. Typically, the dentist will be provided wtih several different tips, and the tip selected will be dependent on the position and orientation of the tooth to be treated. A first configuration of the drill tip 10 is illustrated in FIGS. 1 and 2, and comprises an elongate shaft 20 with a threaded end portion 22 at one end for engagement with the corresponding screw threaded mounting bore 18 in the ultrasonic transducer head, and a hooked end portion or burr 24 at the opposite end for forming a bore of corresponding shape in a tooth root, as will be explained in more detail below. Although in the illustrated embodiment the tip has a screw-threaded projection 22 for coupling to transducer head 12, it will be understood that drill tips with different coupling formations, such as a threaded bore, for example, may be provided for use wtih alternative types of transducer heads. The remainder of the shaft includes an enlarged diameter portion 26 adjacent the threaded end 22, and an elongated, non-straight shaft portion 28 of gradually reducing diameter extending between portion 26 and hooked end portion 24. Enlarged diameter shaft portion 26 has opposing flats 30 for engagement by a wrench for securely fastening the tip 10 to the transducer head and for releasing the tip when replacement with another tip or cleaning is necessary.

Reduced diameter shaft portion 28 includes an angled portion 32 and a straight portion 34, and the hooked end portion 24 extends substantially perpendicular to the straight portion 34, as illustrated in FIG. 1. Hooked end portion 24 has a pointed tip 36.

A second configuration of the drill tip is illustrated in FIGS. 3 to 5. In this configuration, as well as those of FIGS. 6 to 12, the lower portion of the drill tip which is mounted on the transducer head will be identical to that illustrated in FIG. 2 and has therefore been omitted. In each case, it will be understood that the screw threaded end portion may be replaced with other suitable fastener configurations, dependent on the type of coupling configuration provided on the transducer head to be used.

In FIGS. 3 to 5, the drill tip 40 has a reduced diameter, elongate shaft portion 42 extending form enlarged portion 46 with a hooked end 48 at the end of shaft portion 42. In this configuration, the shaft portion 42 has an angled portion 50 from which the hooked end 48 extends perpendicularly, so that the hooked end is at a different angle to the overall central axis of the tool than in the configuration of FIG. 2, and is offset from the tool axis by the angled portion 50, whereas in FIG. 2 the hooked end is not offset from the tool axis but projects at right angles directly from this axis (see FIG. 1). In the drill tip 40, the hooked end 48 is at an angle of less than 90 degrees to the axis of the tool head. In both the configuration of FIG. 2 and that of FIGS. 3 to 5, the hooked end of the drill tip is co-planar wtih the remainder of the shaft (as illustrated in FIG. 5). The hooked end 48 of drill tip 40 has a pointed or sharp end 54 and is of flattened circular cross-section, as illustrated in FIG. 4, and will therefore form a bore of corresponding non-circular cross-section in a tooth root. The remainder of the shaft will be of circular cross-section, as in the previous embodiment.

FIGS. 6 to 8 illustrate another modified drill tip 60 in which the tip has an arcuate shaft portion 62 of circular cross-section extending from enlarged portion 64, and the hooked end 66 extends perpendicular to the plane of the arcuate portion 62 (inwardly into the page in the orientation illustrated in FIG. 6). The hooked end 66 in this configuration is of square cross-section. Other non-circular cross-sections may e used in alternative versions in order to provide an improved retention factor for fillings in the correspondingly non-circular cross-section bores formed by the tips in a tooth root. The tip 68 of the hooked end is pointed, as illustrated in FIG. 7.

FIGS. 9 and 10 illustrate a fourth configuration of the drill tip 70, in which the hooked end 72 is angled or offset in one direction relative to the arcuate shaft portion 74 from which it projects. In the modified tip 80 of FIGS. 11 and 12, the hooked end 82 is angled or offset in the opposite direction from slightly arcuate shaft portion 84. In the configuration of FIGS. 11 and 12, the hooked end 82 is also non-circular and may be of square or hexagonal cross-section, for example. Each of the tips 70 and 80 has a pointed end.

In each of the drill tips illustrated in FIGS. 1 to 12, an elongate, non-straight shaft portion extends between the hooked end of the tool or tip and the enlarged diameter portion which is secured to the hand held transducer head. Preferably, the separation between the hooked end and the transducer head is of the order of 20 to 30 mm, allowing a dental surgeon plenty of room to maneuver the hooked end into the appropriate position in the oral cavity, as will be explained in more detail below. The elongate connecting shaft portion is not straight, but either has portions angled relative to one another or is arcuate, allowing access to posterior regions of the mouth. The tips will be made of a suitable metal as commonly used in dentistry, such as stainless steel. The length of the hooked end is preferably of the order of 3 mm, corresponding to the maximum drilling depth needed to form retro-preparations in tooth roots. The elongate, reduced diameter shaft portion has a diameter of the order of 1 to 2 mm, so that only a small size opening needs to be made in the jawbone for access to a tooth root.

The different configurations of the drill tip allow a dental surgeon to gain access to different areas of the mouth while holding the transducer head at a comfortable angle, and enable the bore in a tooth root to be drilled accurately parallel to the tooth axis, even in the case of severely inclined teeth. FIG. 13 illustrates the use of a selected one of the drill tips in a retro-filling preparation. In FIG. 13, a retro-filling bore is to be made in a root 90 of one of a patient's upper molars 92. From X-rays of the patient's jaw, the dentist can determine the exact location and orientation of the root, and makes a small opening in the jawbone at the appropriate position. The appropriate tip will be selected and attached to the transducer head 12. Typically, tips wtih offset hooked ends will be selected for working in the rear of the jaw, since this will enable the hand-piece to be held at a comfortable, acute angle relative to the patient's teeth as illustrated in FIG. 13, while the hooked end is presented in alignment wtih the central longitudinal axis of the tooth root so that a parallel bore can be drilled. The elongate, reduced diameter, angled or arcuate shaft portion connecting the hooked end to the enlarged diameter end of the drill tip or tool allows access to the root via a relatively small opening in the jawbone, since the angle of the shaft portion enables the tip to extend transversely through the opening with the hooked end in the appropriate orientation.

The straight planar tip illustrated in FIG. 2 will typically be used for working in the front of a patient's mouth where it can be inserted directly through a front opening in the jaw bone. The tip of FIGS. 3 to 5 has a hooked end offset from the axis of the tool, making it convenient for use in the rear of the jaw with teeth having relatively straight roots, as illustrated in FIG. 13. The tips of FIGS. 6 to 12 all have hooked ends which are offset or angled relative to the plane of the arcuate or angled shaft portion of the tip, with the offset angle varying from 90 degrees in the version of FIGS. 6 to 8 down to around 15 or 20 degrees in FIGS. 9 to 12. These tips are suitable for use in the rear of the jaw where the tooth root is inclined inwardly or outwardly relative to the "plane" of the jaw. In each case, the hand-piece of the transducer can be held at a comfortable angle while the hooked end of the tool is presented parallel and co-axial with the root axis to drill an appropriate parallel bore 94 in the tooth for receiving a filling, as illustrated in FIG. 14. If greater retention is required, a tip with a non-circular cross-section at its hooked end will be selected.

Once the appropriate tip has been selected and attached to the ultrasonic transducer head, and inserted through the jawbone opening so that its hooked end is aligned with the tooth root to be drilled, the transducer is switched on, causing ultrasonic vibration in the hooked end of the tool and thus drilling out or excavating a bore in the root. Once the bore has been drilled to the desired depth, the transducer is switched off and the tip is removed from the patient's jaw.

The drilling tool and assembly described above enables a reverse cylindrical bore to be cut in a tooth root cleanly, quickly and accurately through a relatively small opening in the jawbone, reducing the risk of infection. The tip allows a deeper, more parallel and more accurate preparation than with conventional drilling tools for forming retro-preparations, and also allows retro-preparations in severely inclined teeth which would not have been possible using conventional tools.

Although some preferred embodiments of the invention have been described above by way of example only, it will be understood by those skilled in the field that modifications may be made to the disclosed embodiments without departing from the scope of the invention, which is defined by the appended claims.

I claim:

1. A tool for drilling bores in the roots of teeth, comprising:
    an elongate drill member having coupling means at one end for coupling the member to an ultrasonic transducer head, and a hooked portion at the opposite end for forming a bore in a tooth root; and
    an elongate shaft portion which is not straight extending between said coupling means and said hooked portion, said hooked portion projecting at an angle to said elongate shaft portion, and said hooked portion being offset at an angle relative to the plane of the non-straight shaft portion.

2. The tool as claimed in claim 1, wherein the elongate shaft portion includes at least two portions at angles to one another, one of the portions being co-axial with said securing means.

3. The tool as claimed in claim 1, wherein the elongate shaft portion is arcuate along at least part of its length.

4. The tool as claimed in claim 1, wherein the hooked portion is of non-circular cross-section.

5. The tool as claimed in claim 4, wherein the shaft portion is of circular cross-section.

6. The tool as claimed in claim 4, wherein the hooked portion is of square cross-section.

7. The tool as claimed in claim 1, wherein the elongate shaft portion includes a first portion of enlarged diameter and a second portion of reduced diameter extending between said first portion and said hooked portion.

8. The tool as claimed in claim 7, wherein the diameter of said second portion is between 1 and 2 mm.

9. The tool as claimed in claim 1, wherein the end of the hooked portion is pointed.

10. A tool assembly for drilling a bore in a tooth root, comprising:
    an ultrasonic transducer head having first coupling means at one end for securing the head to a member to be vibrated;
    at least two different elongate drill members for selectively securing to said transducer head, each drill member having second coupling means at one end for mating engagement with the transducer head coupling means and a hooked portion at the opposite end for drilling a bore in a tooth root;
    each drill member having an elongate shaft portion extending between said second coupling means and said hooked portion, the hooked portion extending at an angle to said elongate shaft portion and having a pointed end; and
    a first one of said drill members having a hooked portion which is co-planar with the remainder of the tool and a second drill member having a hooked portion which is offset at an angle to the plane of the remainder of the tool.

11. The assembly as claimed in claim 10, including a third drill member with an offset hooked portion angled in the opposite direction to the offset hooked portion of said second drill member.

12. The assembly as claimed in claim 10, including a plurality of drill members of different configurations for selectively securing to said transducer head, said drill members including at least one drill member wtih an elongate shaft portion which is arcuate along at least part of its length, and at least one drill member wtih an elongate shaft portion having portions which are angled relative to one another.

13. The assembly as claimed in claim 10, wherein said drill members have hooked portions of different cross-sectional shape.

14. A method of drilling a dental retro-preparation, comprising the steps of:

securing an elongate drill member having a shaft with a hooked end to an ultrasonic transducer head;

forming an access opening in the jawbone up to the tooth root to be treated;

inserting the hooked end and part of the shaft of the drill member through the access opening until the pointed tip of the hooked end contacts the bottom of the tooth root;

orienting the axis of the hooked end substantially co-axially with the tooth root;

switching on the ultrasonic transducer head to vibrate the hooked end of the tool; and cutting a bore in the tooth root with the ultrasonically vibrating hooked end of the drill member.

* * * * *

REEXAMINATION CERTIFICATE (3154th)

United States Patent [19]

Carr

[11] B1 5,094,617

[45] Certificate Issued Mar. 11, 1997

[54] DENTAL RETRO-FILLING PREPARATION TOOL AND METHOD

[76] Inventor: Gary B. Carr, 273 Church Ave., Chula Vista, Calif. 92010

Reexamination Request:
No. 90/003,920, Aug. 17, 1995

Reexamination Certificate for:
Patent No.: 5,094,617
Issued: Mar. 10, 1992
Appl. No.: 625,360
Filed: Dec. 11, 1990

[51] Int. Cl.⁶ ..................................................... A61C 1/07
[52] U.S. Cl. ........................... 433/119; 433/165; 433/224
[58] Field of Search ........................... 433/102, 118, 433/119, 81, 165, 166, 86, 124, 125, 141

[56] References Cited

U.S. PATENT DOCUMENTS 3,133,351   5/1964   Von Seggern ............................ 433/119
3,703,037   11/1972   Robinson ..................................... 433/86

FOREIGN PATENT DOCUMENTS 597313   5/1960   Canada ................................... 433/119

OTHER PUBLICATIONS

Union Broach 75th–Anniversary Catalog, p. 33, "Retro–Filling Amalgam Pluggers", published in 1983.

*Primary Examiner*—Cary E. O'Connor

[57] ABSTRACT

A drilling tool for dental retro-filling preparation comprises an ultrasonic transducer head and one or more elongate drill members for selectively securing to the transducer head. The or each drill member comprises an elongate shaft having a suitable securing mechanism at one end for coupling to the transducer head and a hooked portion at the opposite end comprising the drilling tip which projects at an angle to the remainder of the shaft. The hooked end portion of the shaft is inserted through an appropriate opening in the jawbone until it is located adjacent the tooth root and aligned with the axis of the root, and the transducer head is switched on to cause ultrasonic vibrations in the tip which cut a bore in the tooth root.

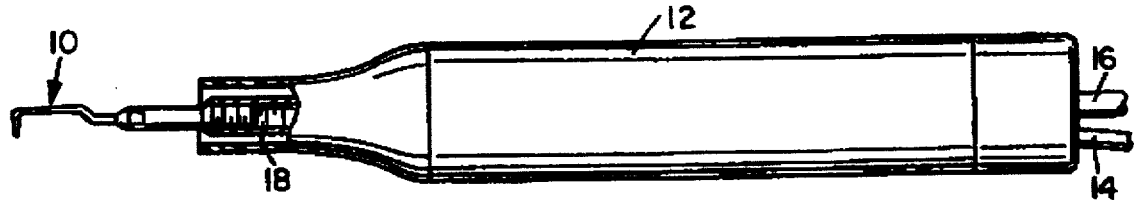

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 2, 9–12 and 14 are determined to be patentable as amended.

Claims 3–8 and 13, dependent on an amended claim, are determined to be patentable.

New claims 15–39 are added and determined to be patentable.

1. A *piezoelectrically vibratable retro-filling preparation* tool for drilling bores in the *bottoms of* roots of teeth, comprising:

an elongate drill member having coupling means at one end for coupling the member to [an] *a piezoelectric* ultrasonic transducer head, and a *straight* hooked portion at the opposite end *terminating at its outer extremity in a point* for forming a bore in a tooth root; and an elongate shaft portion which is not straight extending between said coupling means and said *straight* hooked portion, said hooked portion projecting at an angle to said elongate shaft portion, and said hooked portion being offset at an angle relative to the plane of the nonstraight shaft portion *for retro-filling preparation of teeth*.

2. The tool as claimed in claim 1, wherein the elongate shaft portion includes at least two portions at angles to one another, one of the portions being co-axial with said [securing] *coupling* means.

9. The tool as claimed in claim 1, [wherein the end of the hooked portion is pointed] *further including a hand tool having an overall central axis which is angled relative to said straight hooked end portion and is provided with a piezoelectric ultrasonic transducer which is drivingly coupled to said coupling means at said one end of said elongate drill member.*

10. A *retro-filling preparation* tool assembly for drilling a bore in *the bottom of* a tooth root, *via a smaller access opening in the jawbone than the large opening necessary using a handpiece with an end portion having a short rotary drill bit projecting perpendicularly therefrom,* comprising:

[an] *a hand tool having an overall central axis provided with a* piezoelectric ultrasonic transducer head having first coupling means at one end for securing the head to a *drill* member to be vibrated;

at least two different elongate drill members for selectively securing to said transducer head, each drill member having second coupling means at one *inner* end for mating engagement with the transducer head coupling means and a *straight* hooked portion at the opposite *outer* end for drilling a bore in a tooth root;

each drill member having an elongate *nonstraight* shaft portion extending between said second coupling means and said *straight* hooked portion, *said nonstraight shaft portion including an outer end section, which is angled relative to the overall central axis of said hand tool, connected to said straight hooked portion, and an inner end section connected to said second coupling means,* the *straight* hooked portion extending at an anle to said *outer section of said* elongate shaft portion *and to said overall central axis of said hand tool* and having a pointed end; and a first one of said drill members having a *straight* hooked portion which is co-planar with the remainder of the [tool] *shaft portion of said first drill member for retro-filling preparation of teeth* and a second drill member having a *straight* hooked portion which is offset at an angle to the plane of the remainder of the [tool] *shaft portion of said second drill member for retro-filling preparation of teeth*.

11. The assembly as claimed in claim 10, including a third drill member [with an] *configured to include substantially the same structure as recited in claim 10 for the second drill member, except the* offset hooked portion *thereof is* angled in the opposite direction to the offset hooked portion of said second drill member.

12. The assembly as claimed in claim 10, including a plurality of drill members of different configurations for selectively securing to said transducer head, said drill members including at least one drill member with an elongate shaft portion which is arcuate along at least part of its length, and at least one drill member with an elongate shaft portion having [portions] *substantially straight inner and outer sections* which are angled relative to one another.

14. A method of drilling a dental retro-preparation *for a tooth*, comprising the steps of:

securing *the coupling end of* an elongate drill member, having a *nonstraight* shaft with a *straight, pointed* hooked *outer* end *section provided with an axis angled relative to that portion of the shaft to which it is connected,* to an ultrasonic *piezoelectric* transducer head *of a hand tool to dispose the axis of the hooked end section at an angle relative to the overall axis of the hand tool*;

forming [an] *a smaller* access opening in the *rear of the jawbone up to the tooth root of a tooth in the rear of the jaw* to be treated *than the larger opening necessary using hand tools with an end portion having a short rotary drill bit projecting perpendicularly therefrom*;

inserting the hooked end *section* and part of the shaft of the drill member through the access opening until the pointed tip of the hooked end *section* contacts the bottom of the tooth root *of the tooth to be treated*;

orienting the axis of the hooked end *section* substantially co-axially with the tooth root *of the tooth to be treated*;

switching on the ultrasonic *piezoelectric* transducer head to vibrate the hooked end *section* of the tool; and cutting a bore in the tooth root *of the tooth to be treated* substantially coaxial to the tooth root, with the ultrasonically vibrating hooked end *section* of the drill member.

15. *The method of claim 14 wherein the securing step includes securing the coupling end of an elongate drill member, having a nonstraight shaft with a straight, pointed, hooked outer end section provided with an axis angled relative to a straight portion of the nonstraight shaft to which the end section is connected, to an ultrasonic piezo-* electric transducer head of a hand tool to dispose the axis of the hooked end section and the straight portion of the nonstraight shaft at an angle relative to the overall axis of the hand tool.

16. The method of claim 14 wherein the securing step includes securing the coupling end of an elongate drill member having a nonstraight shaft with a straight, pointed, hooked outer end section provided with an axis angled relative to that portion of the shaft to which it is connected and offset at an angle to the plane of the remainder of the drill member, to an ultrasonic piezoelectric transducer head of a hand tool to dispose the axis of the hooked end section at an angle relative to the overall axis of the hand tool.

17. The method of claim 16 wherein the tooth to be treated is a tooth in the rear of the jaw having a tooth root severely inclined inwardly or outwardly relative to the plane of the jaw, the inserting step includes contacting the pointed tip against the bottom of the tooth root of the tooth in the rear of the jaw which is severely inclined inwardly or outwardly relative to the plane of the jaw, the orienting step includes orienting the axis of the hooked end section substantially coaxially with the severely inclined tooth root of the tooth in the rear of the jaw to be treated, and the cutting step includes cutting a bore in the severely inclined tooth root of the tooth in the rear of the jaw to be treated, substantially coaxially to the severely inclined tooth root, with the ultrasonically vibrating hooked end section of the drill member.

18. The tool of claim 1 wherein the nonstraight elongate shaft portion has an outer section and an inner section, said outer section being connected to said straight hooked portion and said inner section being connected to said coupling means, said hooked portion and said outer section forming an angle not exceeding approximately 90°.

19. The tool of claim 1 wherein the straight, hooked portion has a length not exceeding approximately 3 mm.

20. The tool of claim 1 wherein the straight, hooked portion is approximately 3 mm in length.

21. The tool of claim 1 wherein the hooked portion is offset at an angle to said plane of the nonstraight shaft portion in the approximate range of 15°–90°.

22. The tool of claim 1 wherein the hooked portion is offset at an angle of approximately 90° to said plane of the nonstraight shaft portion.

23. The tool of claim 1 wherein the separation between said one end and said opposite end of said elongate drill member is less than approximately 30 mm.

24. The tool of claim 1 wherein the separation between said one end and said opposite end of said elongate drill member is in the approximate range of 20 mm–30 mm.

25. The tool of claim 1 wherein the separation between said one end and said opposite end of said elongate drill member is approximately 30 mm.

26. The tool of claim 1 wherein said elongate drill member is bent to form said angle between said hooked portion and said elongate shaft portion.

27. The tool of claim 1 wherein said elongate drill member is metal and is bent to form said angle between said hooked portion and said nonstraight elongate shaft portion, and wherein said nonstraight elongate shaft includes interconnected inner and outer sections and at least one bend thereon located between said inner and outer sections to define an angle therebetween exceeding 90°.

28. The tool of claim 27 wherein said inner and outer sections are substantially straight.

29. The tool of claim 27 wherein said outer section is connected to said straight, hooked portion, and said hooked portion and said outer section form an angle not exceeding approximately 90°.

30. The tool of claim 1 wherein said straight, hooked portion and said nonstraight elongate shaft portion are formed of metal which is bent between said straight, hooked portion and said nonstraight elongated shaft portion to form a first angle, said nonstraight elongated shaft portion having interconnected inner and outer sections with a bend therebetween to form a second angle.

31. The tool of claim 30 wherein said inner and outer sections are substantially straight.

32. The tool of claim 30 wherein said first angle does not exceed approximately 90° and said second angle exceeds approximately 90°.

33. The tool of claim 32 wherein said inner and outer sections are substantially straight.

34. The tool of claim 33 wherein said straight, hooked portion has a length not exceeding approximately 3 mm.

35. The tool of claim 33 wherein said straight, hooked portion has a length of approximately 3 mm.

36. The tool of claim 35 wherein the hooked portion is offset at an angle to said plane of the nonstraight shaft portion in the approximate range of 15°–90°.

37. The tool of claim 36 wherein the hooked portion is offset at an angle of approximately 90° to said plane of the nonstraight shaft portion.

38. The tool of claim 37 wherein the separation between said one end and said opposite end of said elongate drill member is in the approximate range of 20 mm–30 mm.

39. The tool of claim 38 wherein said separation is approximately 30 mm.

* * * * *